(12) United States Patent
Rivera

(10) Patent No.: US 10,100,361 B2
(45) Date of Patent: Oct. 16, 2018

(54) METHOD FOR DETECTING CYSTIC FIBROSIS

(71) Applicant: QUEST DIAGNOSTICS INVESTMENTS INCORPORATED, Wilmington, DE (US)

(72) Inventor: Steven Patrick Rivera, Mission View, CA (US)

(73) Assignee: Quest Diagnostics Investments Incorporated, Wilmington, DE (US)

( * ) Notice: Subject to any disclaimer, the term of this patent is extended or adjusted under 35 U.S.C. 154(b) by 204 days.

(21) Appl. No.: 14/774,331

(22) PCT Filed: Mar. 14, 2014

(86) PCT No.: PCT/US2014/027870
§ 371 (c)(1),
(2) Date: Sep. 10, 2015

(87) PCT Pub. No.: WO2014/152822
PCT Pub. Date: Sep. 25, 2014

(65) Prior Publication Data
US 2016/0032385 A1 Feb. 4, 2016

Related U.S. Application Data

(60) Provisional application No. 61/785,862, filed on Mar. 14, 2013.

(51) Int. Cl.
| | | |
|---|---|---|
| C12Q 1/68 | (2018.01) | |
| C12Q 1/6883 | (2018.01) | |
| C12Q 1/6827 | (2018.01) | |
| C12Q 1/6855 | (2018.01) | |

(52) U.S. Cl.
CPC ......... *C12Q 1/6883* (2013.01); *C12Q 1/6827* (2013.01); *C12Q 1/6855* (2013.01); *C12Q 2600/112* (2013.01); *C12Q 2600/156* (2013.01)

(58) Field of Classification Search
None
See application file for complete search history.

(56) References Cited

U.S. PATENT DOCUMENTS

| | | |
|---|---|---|
| 2006/0057593 A1 | 3/2006 | Hantash |
| 2010/0167284 A1 | 7/2010 | Huang et al. |

FOREIGN PATENT DOCUMENTS

| | | |
|---|---|---|
| WO | WO 1992/05252 A1 | 4/1992 |
| WO | WO 2012/083225 A2 | 6/2012 |

OTHER PUBLICATIONS

Voelkerding et al; Clinical Chemistry, vol. 55, pp. 641-658; 2009.*
Treff et al., "Evaluation of targeted next-generation sequencing-based preimplantation genetic diagnosis of monogenic disease," Fertility and Sterility, vol. 99, No. 5, p. 1377, Jan. 2013.
Thermofisher Scientific, "Ion Xpress™ Plus gDNA Fragment Library Preparation User Guide," retrieved from the Internet: https://tools.thermofisher.com/content/sfs/manuals/MAN0009847_IonXpressPlus_gDNAFragLibraryPrep_UG.PDF, Jul. 15, 2016.
Achmann et al., "Next Generation Sequencing with the SOLiD System and Ion Torrent's PGM Sequencer: Amplicon Resequencing of the CFTR gene using multiplexing," retrieved from the Internet: http://www.jsi-medisys.de/sites/default/files/Technical%20Notes/Next_GenerationSequencing_with_the_SOLiD_System_and_Ion_Toreent_PGM.pdf, Jan. 2011.
Multiplicom NV, "Instructions for Use Part 1 Mastr™," retrieved from the Internet: http://www.multiplicom.com/sites/default/files/ifu016_parti_mastr_v14110.pdf, Jan. 2014.
Elliott et al., "Rapid Detection of the ACMG/ACOG-Recommended 23 CTFR Disease-Causing Mutations Using Ion Torrent Semiconductor Sequencing," Journal of Biomolecular Techniques, vol. 23, No. 1, pp. 24-30, Apr. 2012.
Tayoun et al., "A Comprehensive Assay for CFTR Mutational Analysis Using Next-Generation Sequencing," Clinical Chemistry, vol. 59, No. 10, pp. 1481-1488, Jun. 2013.
Hoffmann et al., "DNA bar coding and pyrosequencing to identify rare HIV drug resistance mutations," Nucleic Acids Research, vol. 35, No. 13, p. e91, Jan. 2007.
Metzker, "Sequencing technologies—the next generation," Nature Reviews Genetics, vol. 11, No. 1, pp. 31-46, Jan. 2010.
European Search Report issued in application No. EP 14 76 8702 dated Oct. 21, 2016.
Medvedev et al: "Computational Methods for Discovering Structural Variation with Next-Generation Sequencing", Nature Methods, vol. 6, No. 11s, Nov. 1, 2009, pp. S13-S20, XP055065779.
Xie et al: "CNV-seq, A New Method to Detect Copy Number Variation Using High-Throughput Sequencing", BMC Bioinformatics, vol. 10, No. 1, Mar. 6, 2009, p. 80, XP021047346.
Yoon et al: "Sensitive and Accurate Detection of Copy Number Variants Using Read Depth of Coverage", Genome Research, vol. 19, No. 9, Aug. 5, 2009, pp. 1586-1592, XP055167321.
European Official Communication dated Mar. 27, 2018 as issued in corresponding European Application No. 14768702.4.
Stoerker et al., "Rapid genotyping by MALDI-monitored nuclease selection from probe libraries," Nature Biotechnology, vol. 18, pp. 1213-1216, Nov. 1, 2000.
Trujillano et al., "Next generation diagnostics of cystic fibrosis and CFTR-related disorders by targeted multiplex high-coverage resequencing of CFTR," J. Med. Genet., vol. 50, pp. 455-462, May 17, 2013.
International Search Report dated Oct. 24, 2014 in application No. PCT/US2014/027870.

\* cited by examiner

*Primary Examiner* — Jehanne S Sitton
(74) *Attorney, Agent, or Firm* — Foley & Lardner LLP

(57) ABSTRACT

The present invention relates to methods for simultaneously determining the presence or absence of mutations, deletions, duplications and single nucleotide polymorphisms in a cystic fibrosis transmembrane regulator (CFTR) nucleic acid. Oligo nucleotide primers and kits used to amplify regions of a CFTR nucleic acid for high throughput, massively parallel sequencing and methods of determining an individual's cystic fibrosis status are also disclosed.

17 Claims, No Drawings

Specification includes a Sequence Listing.

SEQUENCE LISTING

```
<160> NUMBER OF SEQ ID NOS: 174

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
acactgacga catggttcta ca                                              22

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
tacggtagca gagacttggt ct                                              22

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
aaaggataga caaggaacac atcctgg                                         27
```

<210> SEQ ID NO 4
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 4
ctaataaagc ttggttcttt tctccgac                                    28

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 5
accttgcaaa cgtaacagga accc                                        24

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 6
cggtggcttc ttctgtcctc ca                                          22

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 7
gtcagaatcg ggaaagggag gtg                                         23

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 8
ggggaaagag caaaaggaag gg                                          22

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 9
gtctttggca ttaggagctt gagc                                        24

<210> SEQ ID NO 10

```
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tcaagtgaat atctgttcct cctctcttt                                    29

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gcacatgcaa cttattggtc ccac                                         24

<210> SEQ ID NO 12
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
atgaaattta atttctctgt ttttcccc                                     28

<210> SEQ ID NO 13
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
aggcttatgc cttctcttta ttgtgag                                      27

<210> SEQ ID NO 14
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
tttgttgaaa ttatctaact ttccatttt c                                  31

<210> SEQ ID NO 15
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
cacctgtttt tgctgtgctt ttattttc                                     28

<210> SEQ ID NO 16
<211> LENGTH: 32
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
tactattaga ttgattgatt gattgattga tt                                    32

<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ctcagatctt ccattccaag atccc                                            25

<210> SEQ ID NO 18
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
cttccctatg cactaatcaa aggaatc                                          27

<210> SEQ ID NO 19
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gctattctga ttctataata tgtttttgct ctc                                   33

<210> SEQ ID NO 20
<211> LENGTH: 37
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (5)..(5)
<223> OTHER INFORMATION: Inosine

<400> SEQUENCE: 20
gagtntattt caaatatgat gaatcctagt gcttggc                               37

<210> SEQ ID NO 21
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
cttttcaaac taattgtaca taaaacaagc atc                                   33
```

<210> SEQ ID NO 22
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
aaacaataac aatagaaaaa cttctaatgg tg                                   32

<210> SEQ ID NO 23
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
tgacctaata atgatgggtt ttatttcc                                        28

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
tttcctggat tatgcctggc ac                                              22

<210> SEQ ID NO 25
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
actaaaagtg actctctaat tttctatttt tgg                                  33

<210> SEQ ID NO 26
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
aatttcttaa ttgtgtgctg aatacaattt tc                                   32

<210> SEQ ID NO 27
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gagaggaaat gtaatttaat ttccattttc                                      30

```
<210> SEQ ID NO 28
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
gcatgaaggt agcagctatt tttatggg                                          28

<210> SEQ ID NO 29
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gctaaaatac gagacatatt gcaataaagt att                                    33

<210> SEQ ID NO 30
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
aaaactagga ttttggtcac ttctaaaatg                                        30

<210> SEQ ID NO 31
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
gaactccaaa atctacagcc agactttag                                         29

<210> SEQ ID NO 32
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
ttctcattag aaggagatgc tcctgtc                                           27

<210> SEQ ID NO 33
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
caatcaactc tatacgaaaa ttttccattg                                        30

<210> SEQ ID NO 34
```

<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 34
tgtccttagt accagattct gagcagg         27

<210> SEQ ID NO 35
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 35
ctcagttaac caaggtcaga acattcac        28

<210> SEQ ID NO 36
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 36
ctgtcttatt gtaatagcca taattctttt attc     34

<210> SEQ ID NO 37
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 37
aaatcaactg tgtcttgttc cattcc          26

<210> SEQ ID NO 38
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 38
tgccaaataa cgatttccta tttgc           25

<210> SEQ ID NO 39
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 39
gtgttttaca tttacgtggg agtagcc         27

<210> SEQ ID NO 40
<211> LENGTH: 30

<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
ttttgaggaa tttgtcatct tgtatattat                                    30

<210> SEQ ID NO 41
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
ctcaccaaca tgttttcttt gatcttac                                      28

<210> SEQ ID NO 42
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
ttgcaatgtt ttctatggaa atatttcac                                     29

<210> SEQ ID NO 43
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
cttactttga aactctgttc cacaaagc                                      28

<210> SEQ ID NO 44
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
gaggttcatt tacgtctttt gtgcatc                                       27

<210> SEQ ID NO 45
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
gtgaaattgt ctgccattct taaaaaca                                      28

<210> SEQ ID NO 46
<211> LENGTH: 24
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 46
gtgaagaaag atgacatctg gccc                                            24

<210> SEQ ID NO 47
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
ccttgtggat ctaaatttca gttgacttg                                       29

<210> SEQ ID NO 48
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
cagaagtgat cccatcactt ttaccttat                                       29

<210> SEQ ID NO 49
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
ttcatacttt cttcttcttt tcttttttgc                                      30

<210> SEQ ID NO 50
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
ctctgtggta tctgaactat cttctctaac tg                                   32

<210> SEQ ID NO 51
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
gatcattact gttctgtgat attatgtgtg g                                    31

<210> SEQ ID NO 52
<211> LENGTH: 24
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 52
ctctggtctg acctgccttc tgtc                                              24

<210> SEQ ID NO 53
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
ccagaaactg ctgaacgaga ggag                                              24

<210> SEQ ID NO 54
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
cagaagaaga ggtgcaagat acaagg                                            26

<210> SEQ ID NO 55
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
catttacctt agcgcttcct ttgcg                                             25

<210> SEQ ID NO 56
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
ctcctccttt tcccgatgat cctag                                             25

<210> SEQ ID NO 57
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
ctctctttag gtccagttgg caacg                                             25

<210> SEQ ID NO 58
<211> LENGTH: 23
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 58
ccttcctcct ctcctccttc gct                                          23

<210> SEQ ID NO 59
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
aattcccccc acccacccct actc                                         24

<210> SEQ ID NO 60
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60 cctttccag aggcgacctc tg                                            22

<210> SEQ ID NO 61
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
ctttcgtggg cacgtgtctt tc                                           22

<210> SEQ ID NO 62
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
ttctcttctc taaataatta ataatatgaa tttctc                             36

<210> SEQ ID NO 63
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
gtgatacata atgaatgtac aaatgagatc c                                 31

<210> SEQ ID NO 64
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 64
gctgggtgta ggagcagtgt cct          23

<210> SEQ ID NO 65
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
catggggcct gtgcaaggaa g          21

<210> SEQ ID NO 66
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
taaccactaa ttactattat ctgacccagg          30

<210> SEQ ID NO 67
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
tttaaaactt tcaagttatg aaaataggtt gc          32

<210> SEQ ID NO 68
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
aaggacagaa ttactaacaa tattgaaatt attg          34

<210> SEQ ID NO 69
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (21)..(21)
<223> OTHER INFORMATION: Inosine

<400> SEQUENCE: 69
gatggtggtg aatatttttcc ngag          24

<210> SEQ ID NO 70
<211> LENGTH: 37
<212> TYPE: DNA

<213> ORGANISM: Artificial Sequence
<220> FEATURE:
<223> OTHER INFORMATION: Description of Artificial Sequence: Synthetic
      primer

<400> SEQUENCE: 70
tatttaaatc atagtatata atgcagcatt atggtac                              37

<210> SEQ ID NO 71
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
gaagaaaaca gttaggtgtt tagagcaaac                                      30

<210> SEQ ID NO 72
<211> LENGTH: 31
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (20)..(20)
<223> OTHER INFORMATION: Inosine

<400> SEQUENCE: 72
cgccattagg atgaaatccn tattcacaaa g                                    31

<210> SEQ ID NO 73
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
aagaagtgag aaattactga agaagaggct                                      30

<210> SEQ ID NO 74
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
caaattaagt tcttaatagt gaagaacaaa agaac                                35

<210> SEQ ID NO 75
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
atcataggaa acaccaaaga tgatattttc                                      30

-continued

<210> SEQ ID NO 76
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 76
ggttcatatg cataatcaaa aagttttcac                                    30

<210> SEQ ID NO 77
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 77
gcaaatgctt gctagaccaa taattag                                       27

<210> SEQ ID NO 78
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 78
gaacagtaat aaagatgaag acacagttcc c                                  31

<210> SEQ ID NO 79
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 79
gcatgagcat tataagtaag gtattcaaag                                    30

<210> SEQ ID NO 80
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 80
ggtactaagg acagccttct ctctaaag                                      28

<210> SEQ ID NO 81
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 81
caaaattaat attttgtcag ctttctttaa atg                                33

<210> SEQ ID NO 82

```
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
gaaagaatca catcccatga gttttg                                          26

<210> SEQ ID NO 83
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
aagattgttt ttttgtttct gtccagg                                         27

<210> SEQ ID NO 84
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
ctaaggacag ccttctctct aaaggc                                          26

<210> SEQ ID NO 85
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
tccttcgtgc ctgaagcgtg g                                               21

<210> SEQ ID NO 86
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
cacttttcgt gtggatgctg ttg                                             23

<210> SEQ ID NO 87
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
gtgaaatacc cccaagcgat gtatac                                          26

<210> SEQ ID NO 88
<211> LENGTH: 35
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
ctttaaatcc agtaatactt tacaatagaa cattc                              35

<210> SEQ ID NO 89
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
acaaagtgga ttacaataca tacaaacata gtg                                33

<210> SEQ ID NO 90
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
gaagaatccc atagcaagca aagtg                                         25

<210> SEQ ID NO 91
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
ggatcagcag tttcatttct tagacctag                                     29

<210> SEQ ID NO 92
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
taataataca gacatactta acggtactta tttttac                            37

<210> SEQ ID NO 93
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
caagatgagt atcgcacatt cactgtc                                       27

<210> SEQ ID NO 94
<211> LENGTH: 28
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 94
caagaaccag ttggcagtat gtaaattc                                        28

<210> SEQ ID NO 95
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
cttaaatgct tagctaaagt taatgagttc atag                                 34

<210> SEQ ID NO 96
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
tttttcataa aagttaaaaa gatgataaga ctt                                  33

<210> SEQ ID NO 97
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
atctttgaca gtcatttggc ccc                                             23

<210> SEQ ID NO 98
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
gtctaacaaa gcaagcagtg ttcaaatc                                        28

<210> SEQ ID NO 99
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
ggtgctagct gtaattgcat tgtacc                                          26

<210> SEQ ID NO 100
<211> LENGTH: 25
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 100
cttttttctg gctaagtcct tttgc                                           25

<210> SEQ ID NO 101
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
cctttcaaaa tcatttcagt tagcagc                                         27

<210> SEQ ID NO 102
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
gtgctattaa gtaacagaac atctgaaact c                                    31

<210> SEQ ID NO 103
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103
aattacaagg gcaatgagat cttaagtaaa g                                    31

<210> SEQ ID NO 104
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 104
tggggaaaga gcttcaccct gt                                              22

<210> SEQ ID NO 105
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 105
gtcccatgtc aacatttatg ctgc                                            24

<210> SEQ ID NO 106
<211> LENGTH: 27
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 106
catatcagtg tcctcaattc cccttac                                          27

<210> SEQ ID NO 107
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 107
cgtgtcctaa gatttctgtg                                                  20

<210> SEQ ID NO 108
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 108
tgccaactgg acctaaag                                                    18

<210> SEQ ID NO 109
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109
cacccagagt agtaggtctt tg                                               22

<210> SEQ ID NO 110
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 110
cataattttc catatgccag                                                  20

<210> SEQ ID NO 111
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 111
cttgggttaa tctccttgga                                                  20

<210> SEQ ID NO 112
<211> LENGTH: 25
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 112
aaagtcttgt gttgaaattc tcagg                                        25

<210> SEQ ID NO 113
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 113
acatttatga acctgagaag                                              20

<210> SEQ ID NO 114
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 114
ggggtggaag atacaatgac                                              20

<210> SEQ ID NO 115
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 115
aaaataatgc ccatctgttg                                              20

<210> SEQ ID NO 116
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 116
cttccattcc aagatccc                                                18

<210> SEQ ID NO 117
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 117
gatgtagcac aatgagagta taaag                                        25

<210> SEQ ID NO 118
<211> LENGTH: 19
<212> TYPE: DNA
<213> ORGANISM: Artificial Sequence
<220> FEATURE:
<223> OTHER INFORMATION: Description of Artificial Sequence: Synthetic
      primer <210> SEQ ID NO 119
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 119
agcagagtac ctgaaacagg a                                           21

<210> SEQ ID NO 120
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 120
cagattgagc atactaaaag tg                                          22

<210> SEQ ID NO 121
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 121
gtgtgctgaa tacaattttc                                             20

<210> SEQ ID NO 122
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 122
gtgaatcgat gtggtgacca                                             20

<210> SEQ ID NO 123
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 123
cgaggataaa tgatttgctc aaag                                        24

<210> SEQ ID NO 124
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 124
tcctaactga gaccttacac                                           20

<210> SEQ ID NO 125
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 125
gtggcatgaa actgtactgt                                           20

<210> SEQ ID NO 126
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 126
atgggaggaa taggtgaaga                                           20

<210> SEQ ID NO 127
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 127
ggttaagggt gcatgctctt c                                         21

<210> SEQ ID NO 128
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 128
ctactgtgat ccaaacttag tattg                                     25

<210> SEQ ID NO 129
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 129
acactttgtc cactttgc                                             18

<210> SEQ ID NO 130
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 130
atctattcaa agaatggcac                                        20

<210> SEQ ID NO 131
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 131
tagatgctgt gatgaactg                                         19

<210> SEQ ID NO 132
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 132
cccgacaaat aaccaagtga c                                      21

<210> SEQ ID NO 133
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 133
gaatcattca gtgggtataa gcag                                   24

<210> SEQ ID NO 134
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 134
tctctattct gttccaagg                                         19

<210> SEQ ID NO 135
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 135
tgatggtaag tacatgggtg                                        20

<210> SEQ ID NO 136
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 136
ctgtcaaggt tgtaaataga c                                              21

<210> SEQ ID NO 137
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 137
ctgttctgtg atattatgtg tg                                             22

<210> SEQ ID NO 138
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 138
tattttcctt tgagcctg                                                  18

<210> SEQ ID NO 139
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 139
cttaattgtg tgctgaatac aattttc                                        27

<210> SEQ ID NO 140
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 140
gaatcattca gtgggtataa gcag                                           24

<210> SEQ ID NO 141
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 141
cctttcccga ttctgactc                                                 19

<210> SEQ ID NO 142
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 142
ccaaacccaa cccatacac                                                 19

<210> SEQ ID NO 143
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 143
caaacccaac ccatacacac                                              20

<210> SEQ ID NO 144
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 144
ctatgtttgc tttctcttct c                                            21

<210> SEQ ID NO 145
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 145
attcaccaga tttcgtagtc                                              20

<210> SEQ ID NO 146
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 146
ccagctcact acctaattta tgacat                                       26

<210> SEQ ID NO 147
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 147
cagaataggg aagctagag                                               19

<210> SEQ ID NO 148
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 148
catagagcag tcctggtttt ac                                           22

<210> SEQ ID NO 149
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 149
gtggaagtct accatgataa acata                               25

<210> SEQ ID NO 150
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 150
gcaaagttca ttagaactga tc                                  22

<210> SEQ ID NO 151
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 151
cacaaagaag aaaacagtta gg                                  22

<210> SEQ ID NO 152
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 152
aaagagacat ggacaccaaa ttaag                               25

<210> SEQ ID NO 153
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 153
ccattcacag tagcttaccc a                                   21

<210> SEQ ID NO 154
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 154
tacatgaatg acatttacag ca                                  22

-continued

```
<210> SEQ ID NO 155
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 155
aagatgaaga cacagttccc                                              20

<210> SEQ ID NO 156
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 156
ctggtttagc atgaggcggt                                              20

<210> SEQ ID NO 157
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 157
tcgtatagag ttgattggat tgaga                                        25

<210> SEQ ID NO 158
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 158
ttctgtgggg tgaaatac                                                18

<210> SEQ ID NO 159
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 159
cacatcccca aactatctta a                                            21

<210> SEQ ID NO 160
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 160
tggattacaa tacatacaaa ca                                           22

<210> SEQ ID NO 161
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 161
ggccctattg atggtggatc                                                  20

<210> SEQ ID NO 162
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 162
aggtaagcag ttctgactta tta                                              23

<210> SEQ ID NO 163
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 163
cagatgagta tcgcacattc                                                  20

<210> SEQ ID NO 164
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 164
gataacctat agaatgcagc                                                  20

<210> SEQ ID NO 165
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 165
gaaggaaaga agagataagg                                                  20

<210> SEQ ID NO 166
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 166
cgctaacaca ttgcttcagg ctac                                             24

<210> SEQ ID NO 167
<211> LENGTH: 19
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 167
cttcaatgca cctcctccc                                               19

<210> SEQ ID NO 168
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 168
acaagtatca aatagcag                                                18

<210> SEQ ID NO 169
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 169
caaaagtacc tgttgctcca                                              20

<210> SEQ ID NO 170
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 170
aagcaggcat aatgattc                                                18

<210> SEQ ID NO 171
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 171
aattacaagg gcaatgag                                                18

<210> SEQ ID NO 172
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 172
gcagaggtaa ctgttccac                                               19

<210> SEQ ID NO 173
<211> LENGTH: 27
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 173
agtaataaag atgaagacac agttccc                                              27

<210> SEQ ID NO 174
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 174
cttcaatgca cctcctccc                                                       19
```

METHOD FOR DETECTING CYSTIC FIBROSIS

FIELD OF THE INVENTION

The present invention relates to methods for simultaneously determining the presence or absence of mutations, deletions, duplications and single nucleotide polymorphisms in a cystic fibrosis transmembrane regulator (CFTR) nucleic acid. Nucleotide sequences (such as for primers) used to amplify regions of a CFTR nucleic acid for high throughput, massively parallel sequencing and methods of determining an individual's cystic fibrosis status are also disclosed.

BACKGROUND OF THE INVENTION

The following description of the background of the invention is provided simply as an aid in understanding the invention and is not admitted to describe or constitute prior art to the invention.

Cystic fibrosis (CF) is the most common severe autosomal recessive genetic disorder in the Caucasian population. It affects approximately 1 in 2,500 live births in North America (Boat et al, The Metabolic Basis of Inherited Disease, 6th ed, pp 2649-2680, McGraw Hill, NY (1989)). Approximately 1 in 25 persons are carriers of the disease. The major symptoms of cystic fibrosis include chronic pulmonary disease, pancreatic exocrine insufficiency, and elevated sweat electrolyte levels. The symptoms are consistent with cystic fibrosis being an exocrine disorder. Although recent advances have been made in the analysis of ion transport across the apical membrane of the epithelium of CF patient cells, it is not clear that the abnormal regulation of chloride channels represents the primary defect in the disease.

The gene for CF has been localized to a 250,000 base pair genomic sequence present on the long arm of chromosome 7. This sequence encodes a membrane-associated protein called the "cystic fibrosis transmembrane regulator" (or "CFTR"). There are greater than 1000 different mutations in the CFTR gene, having varying frequencies of occurrence in the population, presently reported to the Cystic Fibrosis Genetic Analysis Consortium. These mutations exist in both the coding regions (e.g., ΔF508, a mutation found on about 70% of CF alleles, represents a deletion of a phenylalanine at residue 508) and the non-coding regions (e.g., the 5T, 7T, and 9T mutations correspond to a sequence of 5, 7, or 9 thymidine bases located at the splice branch/acceptor site of intron 8) of the CFTR gene. Comparison of the CFTR genomic and cDNA sequences confirms the presence of 27 exons. The exons are numbered 1-27 as shown in NCBI Reference Sequence accession no. NM_000492.3. Each intron is flanked by the consensus GT-AG splice-site sequence as previously reported (Zielenski, et al., (1991) Genomics 10, 214-228).

Methods for detecting CFTR gene mutations have been described. See e.g., Audrezet et al., "Genomic rearrangements in the CFTR gene: extensive allelic heterogeneity and diverse mutational mechanisms" Hum Mutat. 2004 April; 23(4):343-57; PCT WO 1004/040013 A1 and corresponding US application #20040110138; titled "Method for the detection of multiple genetic targets" by Spiegelman and Lem; US patent application No. 20030235834; titled "Approaches to identify cystic fibrosis" by Dunlop et al.; and US patent application No. 20040126760 titled "Novel compositions and methods for carrying out multiple PCR reactions on a single sample" by N. Broude.

Currently, however, multiple different analysis and/or detection methods must be employed in order to accurately obtain comprehensive sequence data. For example, traditional Sanger sequencing methodology may be employed to determine the presence or absence of mutations involving a small number of nucleotides in the CFTR gene. Sanger sequencing, though, is unable to detect large deletions and duplications such as those involving one or more exons. As a result, additional methods such as quantitative fluorescent polymerase chain reaction (QF-PCR) are needed to detect these larger types of mutations.

Accordingly, improved methods are needed to efficiently detect the variety of CFTR gene defects which underlie CF and to simultaneously capture both dosage data (e.g., gene copy number) and sequence data. Moreover, improved methods are needed for detecting rare mutations in the CFTR gene. Ideally, methods that can detect multiple classes of CFTR mutations such as those involving small base changes (e.g., missense mutations, nonsense mutations, small insertions or deletions and/or splice-site mutations) and those involving larger deletions and/or duplications in a single assay are desirable.

SUMMARY OF THE INVENTION

Provided is a method for determining the nucleotide sequence of a sample CFTR nucleic acid, the method comprising (a) producing an adapter-tagged amplicon library by amplifying multiple target segments of the sample CFTR nucleic acid and (b) determining the nucleotide sequences of the target segments by sequencing the amplicons in the amplicon library using high throughput massively parallel sequencing.

Also provided is a method for determining the presence or absence of a CFTR nucleotide sequence variant in a sample CFTR nucleic acid comprising (a) producing an adapter-tagged amplicon library by amplifying multiple target segments of the sample CFTR nucleic acid; (b) determining the nucleotide sequences of the target segments by sequencing the amplicons in the amplicon library using high throughput massively parallel sequencing; (c) comparing each target segment nucleotide sequence determined in step (b) with the corresponding region of a reference CFTR nucleotide sequence; and (d) determining that the sample CFTR nucleic acid has a variant sequence if or when one or more of the target segment sequences is different from the corresponding region of the reference CFTR nucleotide sequence.

A sequence variant is a CFTR sequence that is different from a corresponding region of a reference CFTR nucleic acid sequence. Such differences in the CFTR sequence can include point mutations, insertions deletions and/or duplications or copy number variations (CNV). CNVs are gains and losses of genomic sequence >50 bp between two individuals of a species (Mills et al. 2011, Mapping copy number variation by population-scale genome sequencing, Nature 470: 59-65). Such variations can be determined when using next-generation sequencing by using a read depth (i.e., mapping density) approach if amplification is halted during library generation during the exponential phase of PCR. A normal dosage in relation to all other amplicons for a normal specimen will be one, ½ for a homozygous deletions and 1½ for homozygous duplication.

In some embodiments the reference CFTR nucleic acid sequence comprises a wild type CFTR nucleic acid sequence. In some embodiments the sequence variant comprises a CFTR nucleotide sequence mutation associated with cystic fibrosis.

Another aspect of the present invention provides a method for determining the presence or absence of base changes, gene deletions and gene duplications in a sample CFTR nucleic acid as compared to a reference CFTR nucleotide sequence, said method comprising (a) producing an adapter-tagged amplicon library by amplifying multiple target segments of the sample CFTR nucleic acid, (b) determining the nucleotide sequences of the target segments by sequencing the amplicons using high throughput massively parallel sequencing, (c) comparing each target segment sequence determined in step (b) with the corresponding region of the reference CFTR nucleotide sequence; and (d) determining that one or more base changes, gene deletions and/or gene duplications is present in the sample CFTR nucleic acid if or when one or more of the target segment sequences is different from the corresponding region of the reference CFTR nucleotide sequence. In some embodiments, the reference CFTR sequence consists of or, alternatively, comprises a wild type CFTR nucleic acid sequence.

Another aspect of the present invention provides a method for diagnosing a genetic basis for cystic fibrosis in an individual comprising (a) producing an adapter-tagged amplicon library by amplifying multiple target segments of a CFTR nucleic acid from said individual, (b) determining the nucleotide sequences of the target segments by sequencing the amplicons using high throughput massively parallel sequencing, and (c) determining that the individual has a genetic basis for cystic fibrosis if or when the nucleotide sequence of one or more of the target segments contains a mutation associated with cystic fibrosis. Genetic mutations associated with cystic fibrosis are well known in the art and include both rare and common mutations.

In any of the aspects of the present invention, high throughput massively parallel sequencing may be performed using a read depth approach.

A sample CFTR nucleic acid may be any form of nucleic acid including, for example, genomic DNA, RNA (such as mRNA) or cDNA.

In some embodiments of the above methods, CFTR nucleic acids from more than one sample are sequenced. In some cases all samples are sequenced simultaneously in parallel. In a preferred embodiment, CFTR nucleic acids from at least 5, 10, 20, 30 or 35 up to 40, 45, 48 or 50 different samples are amplified and sequenced using methods of the present invention. All amplicons derived from a single sample may comprise an index sequence that indicates the source from which the amplicon is generated, the index for each sample being different from the indexes from all other samples. As such, the use of indexes permits multiple samples to be pooled per sequencing run and the sample source subsequently ascertained based on the index sequence.

In some embodiments, the Access Array™ System (Fluidigm Corp., San Francisco, Calif.) is used to generate a bar coded (indexed) amplicon library by simultaneously amplifying the CFTR nucleic acids from the samples in one set up. The library that is generated then can be used on a sequencing platform such as, for example, Roche/454™ GS FLX™ sequencing system (Roche, Germany), Ion Torrent™ Ion PGM™ Sequencer (Life Technologies, Carlsbad, Calif.) or MiSeq® Personal Sequencer (Illumina, Inc., San Diego, Calif.).

In some embodiments of the present invention, sample CFTR target segments are amplified using primers that contain an oligonucleotide sequencing adapter to produce adapter-tagged amplicons. In other embodiments, the employed primers do not contain adapter sequences and the amplicons produced are subsequently (i.e. after amplification) ligated to an oligonucleotide sequencing adapter on one or both ends of the amplicons. In some embodiments, all sense amplicons contain the same sequencing adapter and all antisense amplicons contain a sequencing adapter having a different sequence from the sense amplicon sequencing adapter. In some embodiments, only a single stranded sample CFTR nucleic acid is amplified and/or sequenced.

Methods of the present invention may be used to sequence all or part of a CFTR gene or cDNA. In some embodiments, from at least one, two, five, 10 or 20 up to 25 or 28 exons are evaluated. In other embodiments all or a portion of the CFTR promoter region is also evaluated. Some or all CFTR introns may also be evaluated. In one embodiment, the CFTR target segments, when combined, represent the CFTR coding region and all intron/exon junctions, plus from about 100, 500, 750, 900 or 1000 up to about 1000 nucleotides of the CFTR promoter immediately upstream (in the 5 prime direction) of the first exon plus from about 50, 100, 150 or 200 up to about 200, 250, 300 or 400 nucleotides immediately downstream (in the 3 prime direction) of the CFTR gene. In a preferred embodiment, one or more sample CFTR nucleic acids are sequenced using at least one primer that comprise a sequence shown in Table 1 or Table 2. In a preferred embodiment, all of the primers shown in Tables 1 or 2 are used.

In a similar embodiment, all exons and a portion of one or more introns are represented.

Oligonucleotides and combinations of oligonucleotides that are useful as primers in the methods of the present invention are also provided. These oligonucleotides are provided as substantially purified material. Kits comprising oligonucleotides for performing amplifications and sequencing as described herein also are provided.

DETAILED DESCRIPTION OF THE INVENTION

Provided by the present invention are methods for simultaneously determining the presence or absence of CFTR gene mutations involving a small number of nucleotides in addition to larger deletions and duplications in a CFTR nucleotide sequence of a sample CFTR nucleic acid in a single assay. By determining the presence or absence of CFTR nucleotide sequence variants in a sample CFTR nucleic acid, an investigator can determine an individual's cystic fibrosis status based on the presence or absence of CFTR mutations associated with cystic fibrosis in the sample obtained from the individual.

The methods of the present invention comprise generating an adapter-tagged amplicon library by amplifying multiple target segments of a sample CFTR nucleic acid of one or more samples and determining the target segment sequences by sequencing the amplicons using high throughput massively parallel sequencing (i.e., next generation sequencing). Using the provided methods, both gene sequence and gene dosage may be determined in a nucleic acid sample. Gene dosage (also referred to as copy number variation) can be determined by performing next generation sequencing and using a read depth approach.

In some embodiments, the one or more sample CFTR sequences are compared with a reference CFTR sequence to determine if differences (e.g., difference in sequence or copy number) are present. A reference CFTR sequence may be a CFTR genomic or cDNA sequence, or a portion thereof, from a normal (non-cystic fibrosis afflicted and non-cystic fibrosis carrier) individual. In some cases, a reference CFTR sequence may comprise a wild type CFTR nucleic acid sequence. Various methods known in the art (e.g., read depth approach) can be employed to analyze sequencing data to determine if differences are present as compared to a reference sequence.

The term "amplify" as used herein with respect to nucleic acid sequences, refers to methods that increase the representation of a population of nucleic acid sequences in a sample. Nucleic acid amplification methods, such as PCR, isothermal methods, rolling circle methods, etc., are well known to the skilled artisan. See, e.g., Saiki, "Amplification of Genomic DNA" in PCR Protocols, Innis et al., Eds., Academic Press, San Diego, Calif. 1990, pp 13-20; Wharam et al., Nucleic Acids Res. 2001 Jun. 1; 29(11):E54-E54; Hafner et al., Biotechniques 2001 April; 30(4):852-6, 858, 860 passim; Zhong et al., Biotechniques 2001 April; 30(4): 852-6, 858, 860.

The term "CFTR promoter region" as used herein refers to a segment of the CFTR gene representing at least the first 250 nucleotides upstream from the translation start site. In other embodiments, the promoter region may include the first 250 nt, first 300 nt, first 350 nt, first 400 nt, first 450 nt, first 500 nt, first 1 kb, first 5 kb, first 10, kb, first 15, kb, first 20, kb, first 21 kb or first 22 kb of sequence directly upstream of the start codon. A deletion of the promoter region as defined herein may be accompanied by deletion of downstream exons/introns but not all of the CFTR gene. In some embodiments, the coordinate deletion involving the CFTR promoter region and downstream CFTR gene sequence involves about less than 10 exons, and more typically involves less than 5 exons. Deletions or duplications of the CFTR promoter region may be detected using primers that flank the deleted or duplicated sequence. In a preferred embodiment, a promoter deletion or duplication involves a segment of at least four or more nucleotides, more preferably 5 or more, more preferably 8 or more, and even more preferably 12 or more nucleotides.

A "CFTR nucleic acid" as used herein refers to a nucleic acid that contains a sequence of a CFTR gene, mRNA, cDNA or a portion of such a CFTR sequence. A CFTR nucleic acid may contain the CFTR coding region. A CFTR nucleic acid may be genomic DNA, cDNA, single stranded DNA or mRNA. In some embodiments, only a single strand of a sample CFTR nucleic acid is amplified and/or sequenced. In some embodiments both strands of double stranded CFTR DNA are amplified and sequenced. A CFTR nucleic acid may be present in a biological sample or it may be isolated from a biological sample.

The terms "complementary" or "complementarity" as used herein with reference to polynucleotides (i.e., a sequence of nucleotides such as an oligonucleotide or a target nucleic acid) refers to the base-pairing rules. The complement of a nucleic acid sequence as used herein refers to an oligonucleotide which, when aligned with the nucleic acid sequence such that the 5' end of one sequence is paired with the 3' end of the other, is in "antiparallel association." For example, for the sequence "5'-A-G-T-3'" is complementary to the sequence "3'-T-C-A-S." Certain bases not commonly found in natural nucleic acids may be included in the nucleic acids described herein; these include, for example, inosine, 7-deazaguanine, Locked Nucleic Acids (LNA), and Peptide Nucleic Acids (PNA). Complementary need not be perfect; stable duplexes may contain mismatched base pairs, degenerative, or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs. A complement sequence can also be a sequence of RNA complementary to the DNA sequence or its complement sequence, and can also be a cDNA.

The term "deletion" as used herein encompasses a mutation that removes one or more nucleotides from nucleic acid. Conversely, the term "duplication" refers to a mutation that inserts one or more nucleotides of identical sequence directly next to this sequence in the nucleic acid. In a preferred embodiment, a deletion or duplication involves a segment of four or more nucleotides.

The term "dosage" or "gene dosage" refers to the number of copies of a gene, or portions of a gene, present in a sample.

The term "primer" as used herein means a sequence of nucleotides, preferably DNA, that hybridizes to a substantially complementary target sequence and is recognized by DNA polymerase to begin DNA replication. The term primer as used herein includes all forms of primers that may be synthesized including peptide nucleic acid primers, locked nucleic acid primers, phosphorothioate modified primers, labeled primers, and the like.

The term "substantially complementary" as used herein means that two sequences hybridize under stringent hybridization conditions. The skilled artisan will understand that substantially complementary sequences need not hybridize along their entire length. In particular, substantially complementary sequences may comprise a contiguous sequence of bases that do not hybridize to a target sequence, positioned 3' or 5' to a contiguous sequence of bases that hybridize under stringent hybridization conditions to a target sequence.

The term "flanking" as used herein with regard to primers means that a primer hybridizes to a target nucleic acid adjoining a region of interest sought to be amplified on the target. The skilled artisan will understand that preferred primers are pairs of primers that hybridize 5' from a region of interest, one on each strand of a target double stranded DNA molecule, such that nucleotides may be added to the 3' end of the primer by a suitable DNA polymerase. Primers that flank a CFTR exon are generally designed not to anneal to the exon sequence but rather to anneal to sequence that adjoins the exon (e.g. intron sequence). However, in some cases, amplification primer may be designed to anneal to the exon sequence. The location of primer annealing for many primer pairs that may be used with the methods is shown in Table 1.

"Sequencing depth" or "read depth" as used herein refers to the number of times a sequence has been sequenced (the depth of sequencing). As an example, read depth can be determined by aligning multiple sequencing run results and counting the start position of reads in nonoverlapping windows of a certain size (for example, 100 bp). Copy number variation can be determined based on read depth using methods known in the art. For example, using a method described in Yoon et al., Genome Research 2009 September; 19(9): 1586-1592; Xie et al., BMC Bioinformatics 2009 Mar. 6; 10:80; or Medvedev et al., Nature Methods 2009 November; 6(11 Suppl):513-20. Use of this type of method and analysis is referred to as a "read depth approach."

"Coverage depth" refers to the number of nucleotides from sequencing reads that are mapped to a given position.

The term "specific" as used herein in reference to an oligonucleotide primer means that the nucleotide sequence of the primer has at least 12 bases of sequence identity with a portion of the nucleic acid to be amplified when the oligonucleotide and the nucleic acid are aligned. An oligonucleotide primer that is specific for a nucleic acid is one that, under the stringent hybridization or washing conditions, is capable of hybridizing to the target of interest and not substantially hybridizing to nucleic acids which are not of interest. Higher levels of sequence identity are preferred and include at least 75%, at least 80%, at least 85%, at least 90%, at least 95% and more preferably at least 98% sequence identity.

The term "multiplex PCR" as used herein refers to amplification of two or more products which are each primed using a distinct primer pair.

The term "hybridize" as used herein refers to a process where two complementary nucleic acid strands anneal to each other under appropriately stringent conditions. Hybridizations are typically and preferably conducted with probe-length nucleic acid molecules, preferably 20-100 nucleotides in length, more preferably 18-50 nucleotides in length. Nucleic acid hybridization techniques are well known in the art. See, e.g., Sambrook, et al., 1989, Molecular Cloning: A Laboratory Manual, Second Edition, Cold Spring Harbor Press, Plainview, N.Y. Those skilled in the art understand how to estimate and adjust the stringency of hybridization conditions such that sequences having at least a desired level of complementary will stably hybridize, while those having lower complementary will not. For examples of hybridization conditions and parameters, see, e.g., Sambrook, et al., 1989, Molecular Cloning: A Laboratory Manual, Second Edition, Cold Spring Harbor Press, Plainview, N.Y.; Ausubel, F. M. et al. 1994, Current Protocols in Molecular Biology. John Wiley & Sons, Secaucus, N.J. In some embodiments, specific hybridization occurs under stringent hybridization conditions.

The term "stringent hybridization conditions" as used herein refers to hybridization conditions at least as stringent as the following: hybridization in 50% formamide, 5×SSC, 50 mM $NaH_2PO_4$, pH 6.8, 0.5% SDS, 0.1 mg/mL sonicated salmon sperm DNA, and 5× Denhart's solution at 42° C. overnight; washing with 2×SSC, 0.1% SDS at 45° C.; and washing with 0.2×SSC, 0.1% SDS at 45° C. In another example, stringent hybridization conditions should not allow for hybridization of two nucleic acids which differ over a stretch of 20 contiguous nucleotides by more than two bases.

The term "sense strand" as used herein means the strand of double-stranded DNA (dsDNA) that includes at least a portion of a coding sequence of a functional protein. "Antisense strand" means the strand of dsDNA that is the reverse complement of the sense strand.

The term "forward primer" as used herein means a primer that anneals to the anti-sense strand of dsDNA. A "reverse primer" anneals to the sense-strand of dsDNA.

The term "isolated" as used herein with respect to a nucleic acid (e.g., an RNA, DNA or a mixed polymer) is one which is substantially separated from other cellular components which naturally accompany such nucleic acid. The term embraces a nucleic acid sequence which has been removed from its naturally occurring environment, and includes recombinant or cloned DNA isolates, oligonucleotides, and chemically synthesized analogs or analogs biologically synthesized by heterologous systems.

The term "substantially pure" as used herein means a nucleic acid, represents more than 50% of the nucleic acid in a sample. The nucleic acid sample may exist in solution or as a dry preparation.

The term "coding sequence" as used herein means a sequence of a nucleic acid or its complement, or a part thereof, that can be transcribed and/or translated to produce the mRNA for and/or the polypeptide or a fragment thereof. Coding sequences include exons in a genomic DNA or immature primary RNA transcripts, which are joined together by the cell's biochemical machinery to provide a mature mRNA. The anti-sense strand is the complement of such a nucleic acid, and the encoding sequence can be deduced there from.

The term "non-coding sequence" as used herein means a sequence of a nucleic acid or its complement, or a part thereof, that is not transcribed into amino acid in vivo, or where tRNA does not interact to place or attempt to place an amino acid. Non-coding sequences include both intron sequences in genomic DNA or immature primary RNA transcripts, and gene-associated sequences such as promoters, enhancers, silencers, etc.

The term "high throughput, massively parallel sequencing" as used herein refers to sequencing methods that can generate multiple sequencing reactions of clonally amplified molecules and of single nucleic acid molecules in parallel. This allows increased throughput and yield of data. These methods are also known in the art as next generation sequencing (NGS) methods. NGS methods include, for example, sequencing-by-synthesis using reversible dye terminators, and sequencing-by-ligation. Non-limiting examples of commonly used NGS platforms include miRNA BeadArray (Illumina, Inc.), Roche 454™ GS FLX™-Titanium (Roche Diagnostics), and ABI SOLiD™ System (Applied Biosystems, Foster City, Calif.).

The term "carrier state" or "cystic fibrosis carrier" as used herein means a person who contains one CFTR allele that has a mutant CFTR nucleic acid sequence associated with cystic fibrosis, but a second allele that is not a mutant CFTR nucleic acid sequence. Cystic fibrosis is an "autosomal recessive" disease, meaning that a mutation produces little or no phenotypic effect when present in a heterozygous condition with a non-disease related allele, but produces a "disease state" when a person is homozygous or compound heterozygote, i.e., both CFTR alleles are mutant CFTR nucleic acid sequences.

The term "wild type" as used herein with respect to the CFTR gene or a locus thereof refers to the CFTR gene sequence which is found in NCBI GenBank locus IDs M58478 (HUMCFTC), AC000111 and AC000061. A cDNA for a CFTR gene is found in Audrezet et al., Hum. Mutat. (2004) 23 (4), 343-357 and/or Genbank accession number NM_000492.3.

A "rare CFTR mutation" is a mutation in the CFTR gene sequence that is present in <0.1% of cystic fibrosis patients.

A "private CFTR mutation" is a mutation in the CFTR gene sequence that is found in only a single family or a small group.

A "common CFTR mutation" is a mutation in the CFTR gene sequence that is associated with cystic fibrosis and is present in at least 0.1% of patients with cystic fibrosis.

A "genetic basis for cystic fibrosis" in an individual refers to the individual's genotype, in particular, of their CFTR nucleic acids and whether the individual possesses at least one CFTR mutation that contributes to cystric fibrosis.

The term "about" as used herein means in quantitative terms plus or minus 10%.

A "sample CFTR nucleic acid" is a CFTR nucleic acid in, or isolated from, a biological sample. Processing methods to release or otherwise make available a nucleic acid for detection are well known in the art and may include steps of nucleic acid manipulation, e.g., preparing a cDNA by reverse transcription of RNA from the biological sample. A biological sample may be a body fluid or a tissue sample. In some cases a biological sample may consist of or comprise blood, plasma, sera, urine, feces, epidermal sample, vaginal sample, skin sample, cheek swab, sperm, amniotic fluid, cultured cells, bone marrow sample and/or chorionic villi, cultured cells, and the like. Fixed or frozen tissues also may be used. Whole blood samples of about 0.5 to 5 ml collected with EDTA, ACD or heparin as anti-coagulant are suitable. Amniotic fluid of 10-15 ml, cultured cells which are 80-100% confluent in two T-25 flasks and 25 mg of chorionic villi are useful sample amounts for processing.

An "individual" is any mammal. In a preferred embodiment, and individual is a human.

A CFTR target segment that is amplified and sequenced according to the present invention may represent one or more individual exon(s) or portion(s) of exon(s) of the CFTR gene or one or more portions of a CFTR mRNA. A target segment also may include the CFTR promoter region and/or one or more CFTR introns. In some embodiments the target segments represent the entire CFTR gene or the entire CFTR coding region. In a preferred embodiment the target segments represent the entire CFTR coding region and at least one intron or a portion there and an adjacent region located immediately upstream (in the 5' direction) of the coding sequence. The adjacent, upstream region may consist of from about 100 nucleotides up to about 500, 750, 1000, 1100, or 1200 nucleotides of the sequence located immediately upstream of the CFTR coding sequence. In some embodiments, the adjacent, upstream region comprises all or a portion of the CFTR promoter sequence.

In accordance with the present invention, each CFTR nucleic acid target segment may be amplified with an oligonucleotide primer or primer pair specific to the target segment. In some embodiments a single primer or one or both primers of a primer pair comprise a specific adapter sequence (also referred to as a sequencing adapter) ligated to the 5' end of the target specific sequence portion of the primer. This sequencing adapter is a short oligonucleotide of known sequence that can provide a priming site for both amplification and sequencing of the adjoining, unknown nucleic acid. As such, adapters allow binding of a fragment to a flow cell for next generation sequencing. Any adapter sequence may be included in a primer used in the present invention.

In some embodiments, all forward amplicons (i.e., amplicons extended from forward primers that hybridized with antisense strands of a target segment) contain the same adapter sequence. In some embodiments when double stranded sequencing is performed, all forward amplicons contain the same adapter sequence and all reverse amplicons (i.e., amplicons extended from reverse primers that hybridized with sense strands of a target segment) contain an adapter sequence that is different from the adapter sequence of the forward amplicons.

In a particular embodiment, the "forward" adapter sequence consists of or comprises: ACACTGACGACATGGTTCTACA (SEQ ID NO:1) or a sequence 90%, 95% or 99% identical to SEQ ID NO:2. and the reverse adapter sequence consists of or comprises TACGGTAGCAGAGACTTGGTCT (SEQ ID NO:2) or a sequence 90%, 95% or 99% identical to SEQ ID NO:2.

Other adapter sequences are known in the art. Some manufacturers recommend specific adapter sequences for use with the particular sequencing technology and machinery that they offer.

In some cases, amplicons from a single sample source further comprise an identical index sequence (also referred to as an index tag, a "barcode" or a multiplex identifier (MID). In some cases, indexed amplicons are generated using primers (for example, forward primers and/or reverse primers) containing the index sequence. Such indexed primers may be included during library preparation as a "barcoding" tool to identify specific amplicons as originating from a particular sample source. Indexed amplicons from more than one sample source are quantified individually and then pooled prior to sequencing. As such, the use of index sequences permits multiple samples (i.e., samples from more than one sample source) to be pooled per sequencing run and the sample source subsequently ascertained based on the index sequence.

When adapter-ligated and/or indexed primers are employed to amplify a CFTR target segment, the adapter sequence and/or index sequence gets incorporated into the amplicon (along with the target-specific primer sequence) during amplification. Therefore, the resulting amplicons are sequencing-competent and do not require the traditional library preparation protocol. Moreover, the presence of the index tag permits the differentiation of sequences from multiple sample sources.

In some embodiments, sequencing templates (amplicons) are prepared by emulsion-based clonal amplification of target segments using specialized fusion primers (containing an adapter sequence) and capture beads. A single adapter-bound fragment is attached to the surface of a bead, and an oil emulsion containing necessary amplification reagents is formed around the bead/fragment component. Parallel amplification of millions of beads with millions of single strand fragments produces a sequencer-ready library.

In some embodiments the amplicons constituting the adapter-tagged (and, optionally, indexed) amplicon library are produced by polymerase chain reaction (PCR). In some embodiments, the amplicon library is generated using a multiplexed PCR approach, such as that disclosed in U.S. Pat. No. 8,092,996, incorporated by reference herein in its entirety.

Bridge PCR is yet another method for in vitro clonal amplification after a library is generated, in preparation for sequencing. This process is a means to clonally amplify a single target molecule, a member of a library, in a defined physical region such as a solid surface, for example, a bead in suspension or a cluster on a glass slide. In this method, fragments are amplified using primers attached to the solid surface forming "DNA colonies" or "DNA clusters". This method is used in some of the genome analyzer sequencers manufactured by Illumina, Inc. (San Diego, Calif.).

Alternatively, each CFTR nucleic acid target segment may be amplified with non-adapter-ligated and/or non-indexed primers and a sequencing adapter and/or an index sequence may be subsequently ligated to each of the resulting amplicons.

Following the production of an adapter tagged and, optionally indexed, amplicon library, the amplicons are sequenced using high throughput, massively parallel sequencing (i.e. next generation sequencing). Methods for performing high throughput, massively parallel sequencing are known in the art. The capacity offered by next generation sequencing has revolutionized amplicon sequencing. Companies such as RainDance Technologies, Inc. (Lexington, Mass.) and Fluidigm Corporation offer platforms which generate libraries that are sequencing-competent and composed purely of targeted sequences. By enabling high-throughput, mini PCR setup, these technologies are ideal for preparing amplicon libraries. One drawback of PCR-based approaches is the limitation of amplicon length, which is determined by PCR itself. However, by targeting overlapping regions, this problem can be circumvented.

In some embodiments, high throughput, massively parallel sequencing employs sequencing-by-synthesis with reversible dye terminators. In other embodiments, sequencing is performed via sequencing-by-ligation. In yet other embodiments, sequencing is single molecule sequencing.

Sequencing by synthesis, like the "old style" dye-termination electrophoretic sequencing, relies on incorporation of nucleotides by a DNA polymerase to determine the base sequence. Reversible terminator methods use reversible versions of dye-terminators, adding one nucleotide at a time, detecting fluorescence at each position by repeated removal of the blocking group to allow polymerization of another nucleotide. The signal of nucleotide incorporation can vary with fluorescently labeled nucleotides, phosphate-driven light reactions and hydrogen ion sensing having all been used. The MiSeq® personal sequencing system (Illumina, Inc.) employs sequencing by synthesis with reversible terminator chemistry.

In contrast to the sequencing by synthesis method, the sequencing by ligation method uses a DNA ligase to determine the target sequence. This sequencing method relies on enzymatic ligation of oligonucleotides that are adjacent through local complementarity on a template DNA strand. This technology employs a partition of all possible oligonucleotides of a fixed length, labeled according to the sequenced position. Oligonucleotides are annealed and ligated and the preferential ligation by DNA ligase for matching sequences results in a dinucleotide encoded color space signal at that position (through the release of a fluorescently labeled probe that corresponds to a known nucleotide at a known position along the oligo). This method is primarily used by Life Technologies' SOLiD™ sequencers.

The Ion Torrent™ (Life Technologies, Carlsbad, Calif.) amplicon sequencing system employs a flow-based approach that detects pH changes caused by the release of hydrogen ions during incorporation of unmodified nucleotides in DNA replication. For use with this system, a sequencing library is initially produced by generating DNA fragments flanked by sequencing adapters. These fragments are clonally amplified on particles by emulsion PCR. The particles with the amplified template are then placed in a silicon semiconductor sequencing chip. During replication, the chip is flooded with one nucleotide after another, and if a nucleotide complements the DNA molecule in a particular microwell of the chip, then it will be incorporated. A proton is naturally released when a nucleotide is incorporated by the polymerase in the DNA molecule, resulting in a detectable local change of pH. The pH of the solution then changes in that well and is detected by the ion sensor.

The 454™ GS FLX™ sequencing system (Roche, Germany), employs a light-based detection methodology in a large-scale parallel pyrosequencing system. Pyrosequencing uses DNA polymerization, adding one nucleotide species at a time and detecting and quantifying the number of nucleotides added to a given location through the light emitted by the release of attached pyrophosphates. For use with the 454™ system, adapter-ligated DNA fragments are fixed to small DNA-capture beads in a water-in-oil emulsion and amplified by PCR (emulsion PCR). Each DNA-bound bead is placed into a well on a picotiter plate and sequencing reagents are delivered across the wells of the plate. The four DNA nucleotides are added sequentially in a fixed order across the picotiter plate device during a sequencing run. During the nucleotide flow, millions of copies of DNA bound to each of the beads are sequenced in parallel. When a nucleotide complementary to the template strand is added to a well, the nucleotide is incorporated onto the existing DNA strand, generating a light signal that is recorded by a CCD camera in the instrument.

In some embodiments, amplicons from more than one sample source are pooled prior to high throughput sequencing. "Multiplexing" is the pooling of multiple adapter-tagged and indexed libraries into a single sequencing run. When indexed primer sets are used, this capability can be exploited for comparative studies. In some embodiments, amplicon libraries from up to 48 separate sources are pooled prior to sequencing.

The described methods for determining the presence or absence of base changes, gene deletions and gene duplications in a CFTR nucleic acid may be used for determining a genetic basis for cystic fibrosis. Accordingly, one aspect of the present invention provides a method for diagnosing a genetic basis for cystic fibrosis in an individual comprising (a) producing an adapter-tagged amplicon library by amplifying multiple target segments of a sample CFTR nucleic acid from said individual, (b) determining the nucleotide sequences of the target segments by sequencing the amplicons using high throughput massively parallel sequencing, and (c) determining that the individual has a genetic basis for being affected with cystic fibrosis or for being a cystic fibrosis carrier if or when the nucleotide sequence of one or more of the target segments contains a mutation associated with cystic fibrosis.

The present invention can additionally be used to detect one or more rare CFTR mutations or private mutations in a CFTR nucleic acid from an individual, thereby identifying an individual who possesses one or more rare or private CFTR mutation(s). In some embodiments, the present invention is used to identify rare familial mutations in an obligate cystic fibrosis carrier after the carrier has tested negative in a routine screening test for common mutations. Such routine screening tests may include Cystic Fibrosis Screen: Detectable Mutations, CF Mutation Screen, Cystic Fibrosis Mutation Screen, CFTR Screen, Cystic Fibrosis Screen, Cystic Fibrosis Carrier Screen, and CF-60. The present invention can also be used to identify rare mutations in a cystic fibrosis-affected (i.e. symptomatic) individual who has not had two CFTR sequence mutations identified by at least one routine cystic fibrosis mutation screening test.

In some embodiments, the methods disclosed herein are employed to confirm cystic fibrosis carrier status in an individual such as, for example, a parent, a sibling or other relatives of a cystic fibrosis-affected individual with one or more rare or private mutations. In some embodiments, the present invention is used for prenatal diagnosis of an individual, in particular, an individual who is related to a cystic fibrosis-affected individual or who is suspected of being a cystic fibrosis carrier In some aspects of the present invention, at least 2, 5, 10, 20, 25, or 28 and up to 25, 29, or 30, target segments of the CFTR gene may be sequenced with gains and losses of genomic sequence (>50 bp) determined using a read depth approach. In one approach, 29 target segments are sequenced, representing the CFTR coding region (including all exons/intron junctions). In another embodiment, the CFTR coding region (including all exons/intron junctions) in addition to about 1 kb upstream and about 300 kb downstream of the CFTR gene are assayed.

The sequence of substantially pure nucleic acid primers which are DNA (or an RNA equivalent) and which are useful for amplifying the promoter region, all of the CFTR exons and intron/exon junctions, and a region immediately downstream of the CFTR gene are shown in Table 1. The letter F or R at the end of the primer name indicates whether the primer is a forward (F) or reverse (R) PCR primer. In some embodiments, the primers of Table 1 are used with Ion Torrent Personal Genome Machine™ and/or Illumina MiSeq® Personal Sequencing System. In some embodiments, the primers of Table 2 are used with a Roche/454™ GS FLX™ sequencer and/or Sanger sequencing. In a preferred embodiment, one or more primers consisting of or comprising any of SEQ ID NOs: 3-54 and 107-140 further comprise sequencing adapter sequence SEQ ID NO:1. In another preferred embodiment, one or more primers consisting of or comprising any of SEQ ID NOs: 55-106 and 141-174 further comprises sequencing adapter sequence SEQ ID NO:2.

TABLE 1

CFTR Primer Sequences for Amplicon Sequencing

| SEQ ID NO: | Primer Name | Primer Sequence | Hybridizes to |
|---|---|---|---|
| 3 | P1F | AAAGGATAGACAAGGAACACATCCTGG | promoter |
| 4 | P2F | CTAATAAAGCTTGGTTCTTTTCTCCGAC | promoter |
| 5 | P3F | ACCTTGCAAACGTAACAGGAACCC | promoter |
| 6 | P4F | CGGTGGCTTCTTCTGTCCTCCA | promoter |
| 7 | P5F | GTCAGAATCGGGAAAGGGAGGTG | promoter |
| 8 | P6F | GGGGAAAGAGCAAAAGGAAGGG | promoter |
| 9 | E1F | GTCTTTGGCATTAGGAGCTTGAGC | Exon 1 |
| 10 | E2F | TCAAGTGAATATCTGTTCCTCCTCTCTTT | Exon 2 |
| 11 | E3F | GCACATGCAACTTATTGGTCCCAC | Exon 3 |
| 12 | E4aF | ATGAAATTTAATTTCTCTGTTTTTCCCC | Exon 4 |
| 13 | E4bF | AGGCTTATGCCTTCTCTTTATTGTGAG | Exon 4 |
| 14 | E5F | TTTGTTGAAATTATCTAACTTTCCATTTTTC | Exon 5 |
| 15 | E6F | CACCTGTTTTTGCTGTGCTTTTATTTTC | Exon 6 |
| 16 | E7F | TACTATTAGATTGATTGATTGATTGATT | Exon 7 |
| 17 | E8aF | CTCAGATCTTCCATTCCAAGATCCC | Exon 8 |
| 18 | E8bF | CTTCCCTATGCACTAATCAAAGGAATC | Exon 8 |
| 19 | E9F | GCTATTCTGATTCTATAATATGTTTTTGCTCTC | Exon 9 |
| 20 | E9outerF | GAGTTTATTTCAAATATGATGAATCCTAGTGCTTGGC | Exon 9 |
| 21 | E10aF | CTTTTCAAACTAATTGTACATAAAACAAGCATC | Exon 10 |
| 22 | E10bF | AAACAATAACAATAGAAAAACTTCTAATGGTG | Exon 10 |
| 23 | E11aF | TGACCTAATAATGATGGGTTTTATTTCC | Exon 11 |
| 24 | E11bF | TTTCCTGGATTATGCCTGGCAC | Exon 11 |
| 25 | E12F | ACTAAAAGTGACTCTCTAATTTTCTATTTTTGG | Exon 12 |
| 26 | I12F | AATTTCTTAATTGTGTGCTGAATACAATTTTC | Intron 12 |
| 27 | E13F | GAGAGGAAATGTAATTTAATTTCCATTTTC | Exon 13 |
| 28 | 14CFz | GCATGAAGGTAGCAGCTATTTTTATGGG | Exon 14 |
| 29 | E14aF | GCTAAAATACGAGACATATTGCAATAAAGTATT | Exon 14 |
| 30 | E14bF | AAAACTAGGATTTTGGTCACTTCTAAAATG | Exon 14 |
| 31 | E14cF | GAACTCCAAAATCTACAGCCAGACTTTAG | Exon 14 |
| 32 | E14dF | TTCTCATTAGAAGGAGATGCTCCTGTC | Exon 14 |
| 33 | E14eF | CAATCAACTCTATACGAAAATTTTCCATTG | Exon 14 |
| 34 | E14fF | TGTCCTTAGTACCAGATTCTGAGCAGG | Exon 14 |

TABLE 1-continued

CFTR Primer Sequences for Amplicon Sequencing

| SEQ ID NO: | Primer Name | Primer Sequence | Hybridizes to |
|---|---|---|---|
| 35 | E14gF | CTCAGTTAACCAAGGTCAGAACATTCAC | Exon 14 |
| 36 | E15F | CTGTCTTATTGTAATAGCCATAATTCTTTTATTC | Exon 15 |
| 37 | E16F | AAATCAACTGTGTCTTGTTCCATTCC | Exon 16 |
| 38 | E17aF | TGCCAAATAACGATTTCCTATTTGC | Exon 17 |
| 39 | E17bF | GTGTTTTACATTTACGTGGGAGTAGCC | Exon 17 |
| 40 | E18F | TTTTGAGGAATTTGTCATCTTGTATATTAT | Exon 18 |
| 41 | E19F | CTCACCAACATGTTTTCTTTGATCTTAC | Exon 19 |
| 42 | E20aF | TTGCAATGTTTTCTATGGAAATATTTCAC | Exon 20 |
| 43 | E20bF | CTTACTTTGAAACTCTGTTCCACAAAGC | Exon 20 |
| 44 | E21F | GAGGTTCATTTACGTCTTTTGTGCATC | Exon 21 |
| 45 | E22aF | GTGAAATTGTCTGCCATTCTTAAAAACA | Exon 22 |
| 46 | E22bF | GTGAAGAAAGATGACATCTGGCCC | Exon 22 |
| 47 | I22F | CCTTGTGGATCTAAATTTCAGTTGACTTG | Intron 22 |
| 48 | E23F | CAGAAGTGATCCCATCACTTTTACCTTAT | Exon 23 |
| 49 | E24F | TTCATACTTTCTTCTTCTTTTCTTTTTTGC | Exon 24 |
| 50 | E25F | CTCTGTGGTATCTGAACTATCTTCTCTAACTG | Exon 25 |
| 51 | E26F | GATCATTACTGTTCTGTGATATTATGTGTGG | Exon 26 |
| 52 | E27aF | CTCTGGTCTGACCTGCCTTCTGTC | Exon 27 |
| 53 | E27bF | CCAGAAACTGCTGAACGAGAGGAG | Exon 27 |
| 54 | 3UF | CAGAAGAAGAGGTGCAAGATACAAGG | 3' UTR |
| 55 | P1R | CATTTACCTTAGCGCTTCCTTTGCG | promoter |
| 56 | P2R | CTCCTCCTTTTCCCGATGATCCTAG | promoter |
| 57 | P3R | CTCTCTTTAGGTCCAGTTGGCAACG | promoter |
| 58 | P4R | CCTTCCTCCTCTCCTCCTTCGCT | promoter |
| 59 | P5R | AATTCCCCCCACCCACCCCTACTC | promoter |
| 60 | P6R | CCTTTTCCAGAGGCGACCTCTG | promoter |
| 61 | E1R | CTTTCGTGGGCACGTGTCTTTC | Exon 1 |
| 62 | E2R | TTCTCTTCTCTAAATAATTAATAATATGAATTTCTC | Exon 2 |
| 63 | E3R | GTGATACATAATGAATGTACAAATGAGATCC | Exon 3 |
| 64 | E4aR | GCTGGGTGTAGGAGCAGTGTCCT | Exon 4 |
| 65 | E4bR | CATGGGGCCTGTGCAAGGAAG | Exon 4 |
| 66 | E5R | TAACCACTAATTACTATTATCTGACCCAGG | Exon 5 |
| 67 | E6R | TTTAAAACTTTCAAGTTATGAAAATAGGTTGC | Exon 6 |
| 68 | E7R | AAGGACAGAATTACTAACAATATTGAAATTATTG | Exon 7 |
| 69 | E8ar | GATGGTGGTGAATATTTTCCTGAG | Exon 8 |
| 70 | E8br | TATTTAAATCATAGTATATAATGCAGCATTATGGTAC | Exon 8 |
| 71 | E9R | GAAGAAAACAGTTAGGTGTTTAGAGCAAAC | Exon 9 |

TABLE 1-continued

CFTR Primer Sequences for Amplicon Sequencing

| SEQ ID NO: | Primer Name | Primer Sequence | Hybridizes to |
|---|---|---|---|
| 72 | E9outerR | CGCCATTAGGATGAAATCCTTATTCACAAAG | Exon 9 |
| 73 | E10aR | AAGAAGTGAGAAATTACTGAAGAAGAGGCT | Exon 10 |
| 74 | E10bR | CAAATTAAGTTCTTAATAGTGAAGAACAAAAGAAC | Exon 10 |
| 75 | E11aR | ATCATAGGAAACACCAAAGATGATATTTTC | Exon 11 |
| 76 | E11bR | GGTTCATATGCATAATCAAAAAGTTTTCAC | Exon 11 |
| 77 | E12R | GCAAATGCTTGCTAGACCAATAATTAG | Exon 12 |
| 78 | I12R | GAACAGTAATAAAGATGAAGACACAGTTCCC | Intron 12 |
| 79 | E13R | GCATGAGCATTATAAGTAAGGTATTCAAAG | Exon 13 |
| 80 | 14DRz | GGTACTAAGGACAGCCTTCTCTCTAAAG | Exon 14 |
| 81 | E14aR | CAAAATTAATATTTTGTCAGCTTTCTTTAAATG | Exon 14 |
| 82 | E14bR | GAAAGAATCACATCCCATGAGTTTTG | Exon 14 |
| 83 | E14cR | AAGATTGTTTTTTTGTTTCTGTCCAGG | Exon 14 |
| 84 | E14dR | CTAAGGACAGCCTTCTCTCTAAAGGC | Exon 14 |
| 85 | E14eR | TCCTTCGTGCCTGAAGCGTGG | Exon 14 |
| 86 | E14fR | CACTTTTCGTGTGGATGCTGTTG | Exon 14 |
| 87 | E14gR | GTGAAATACCCCCAAGCGATGTATAC | Exon 14 |
| 88 | E15R | CTTTAAATCCAGTAATACTTTACAATAGAACATTC | Exon 15 |
| 89 | E16R | ACAAAGTGGATTACAATACATACAAACATAGTG | Exon 16 |
| 90 | E17aR | GAAGAATCCCATAGCAAGCAAAGTG | Exon 17 |
| 91 | E17bR | GGATCAGCAGTTTCATTTCTTAGACCTAG | Exon 17 |
| 92 | E18R | TAATAATACAGACATACTTAACGGTACTTATTTTTAC | Exon 18 |
| 93 | E19R | CAAGATGAGTATCGCACATTCACTGTC | Exon 19 |
| 94 | E20aR | CAAGAACCAGTTGGCAGTATGTAAATTC | Exon 20 |
| 95 | E20bR | CTTAAATGCTTAGCTAAAGTTAATGAGTTCATAG | Exon 20 |
| 96 | E21R | TTTTTCATAAAAGTTAAAAAGATGATAAGACTT | Exon 21 |
| 97 | E22aR | ATCTTTGACAGTCATTTGGCCCC | Exon 22 |
| 98 | E22bR | GTCTAACAAAGCAAGCAGTGTTCAAATC | Exon 22 |
| 99 | I22R | GGTGCTAGCTGTAATTGCATTGTACC | Intron 22 |
| 100 | E23R | CTTTTTTCTGGCTAAGTCCTTTTGC | Exon 23 |
| 101 | E24R | CCTTTCAAAATCATTTCAGTTAGCAGC | Exon 24 |
| 102 | E25R | GTGCTATTAAGTAACAGAACATCTGAAACTC | Exon 25 |
| 103 | E26R | AATTACAAGGGCAATGAGATCTTAAGTAAAG | Exon 26 |
| 104 | E27aR | TGGGGAAAGAGCTTCACCCTGT | Exon 27 |
| 105 | E27bR | GTCCCATGTCAACATTTATGCTGC | Exon 27 |
| 106 | 3UR | CATATCAGTGTCCTCAATTCCCCTTAC | 3' UTR |

TABLE 2

CFTR Primer Sequences for Amplicon Sequencing

| SEQ ID NO: | Primer Name | Primer Sequence | Hybridizes to |
|---|---|---|---|
| 107 | q-PROMOTER-1-1F | CGTGTCCTAAGATTTCTGTG | promoter |
| 108 | q-PROMOTER-2-1F | TGCCAACTGGACCTAAAG | promoter |
| 109 | q1e1F | CACCCAGAGTAGTAGGTCTTTG | Exon 1 |
| 110 | q2e2F | CATAATTTTCCATATGCCAG | Exon 2 |
| 111 | s3e1F | CTTGGGTTAATCTCCTTGGA | Exon 3 |
| 112 | q4e1F | AAAGTCTTGTGTTGAAATTCTCAGG | Exon 4 |
| 113 | q5e3F | ACATTTATGAACCTGAGAAG | Exon 5 |
| 114 | q6ae1F | GGGGTGGAAGATACAATGAC | Exon 6 |
| 115 | q6be2F | AAAATAATGCCCATCTGTTG | Exon 7 |
| 116 | q7e3F | CTTCCATTCCAAGATCCC | Exon 8 |
| 117 | q8e1F | GATGTAGCACAATGAGAGTATAAAG | Exon 9 |
| 118 | q9e9F | TGGATCATGGGCCATGTGC | Exon 10 |
| 119 | s10e3F | AGCAGAGTACCTGAAACAGGA | Exon 11 |
| 120 | q11e1F | CAGATTGAGCATACTAAAAGTG | Exon 12 |
| 121 | q11i4F | GTGTGCTGAATACAATTTTC | Intron 12 |
| 122 | s12e1F | GTGAATCGATGTGGTGACCA | Exon 13 |
| 123 | q13-1e1F | CGAGGATAAATGATTTGCTCAAAG | Exon 14 |
| 124 | q13-2e1F | TCCTAACTGAGACCTTACAC | Exon 14 |
| 125 | q14ae5F | GTGGCATGAAACTGTACTGT | Exon 15 |
| 126 | q14be2F | ATGGGAGGAATAGGTGAAGA | Exon16 |
| 127 | q15e3F | GGTTAAGGGTGCATGCTCTTC | Exon 17 |
| 128 | q16e4F | CTACTGTGATCCAAACTTAGTATTG | Exon 18 |
| 129 | q17ae1F | ACACTTTGTCCACTTTGC | Exon 19 |
| 130 | q17be1F | ATCTATTCAAAGAATGGCAC | Exon 20 |
| 131 | q18e1F | TAGATGCTGTGATGAACTG | Exon 21 |
| 132 | q19e3F | CCCGACAAATAACCAAGTGAC | Exon 22 |
| 133 | q19i2F | GAATCATTCAGTGGGTATAAGCAG | Intron 22 |
| 134 | q20e3F | TCTCTATTCTGTTCCAAGG | Exon 23 |
| 135 | q21e1F | TGATGGTAAGTACATGGGTG | Exon 24 |
| 136 | q22e1F | CTGTCAAGGTTGTAAATAGAC | Exon 25 |
| 137 | q23e1F | CTGTTCTGTGATATTATGTGTG | Exon 26 |
| 138 | q24e1F | TATTTTCCTTTGAGCCTG | Exon 27 |
| 139 | CFTR-22.2F | CTTAATTGTGTGCTGAATACAATTTTC | Intron 12 |
| 140 | CFTR-31.2F | GAATCATTCAGTGGGTATAAGCAG | Intron 22 |
| 141 | q-PROMOTER-1-1R | CCTTTCCCGATTCTGACTC | promoter |

TABLE 2-continued

CFTR Primer Sequences for Amplicon Sequencing

| SEQ ID NO: | Primer Name | Primer Sequence | Hybridizes to |
|---|---|---|---|
| 142 | q-PROMOTER-2-1R | CCAAACCCAACCCATACAC | promoter |
| 143 | q1e1R | CAAACCCAACCCATACACAC | Exon 1 |
| 144 | q2e2R | CTATGTTTGCTTTCTCTTCTC | Exon 2 |
| 145 | s3e2R | ATTCACCAGATTTCGTAGTC | Exon 3 |
| 146 | q4e1R | CCAGCTCACTACCTAATTTATGACAT | Exon 4 |
| 147 | q5e4R | CAGAATAGGGAAGCTAGAG | Exon 5 |
| 148 | q6ae1R | CATAGAGCAGTCCTGGTTTTAC | Exon 6 |
| 149 | q6be2R | GTGGAAGTCTACCATGATAAACATA | Exon 7 |
| 150 | q7E4R | GCAAAGTTCATTAGAACTGATC | Exon 8 |
| 151 | q8e1R | CACAAAGAAGAAACAGTTAGG | Exon 9 |
| 152 | q9e11R | AAAGAGACATGGACACCAAATTAAG | Exon 10 |
| 153 | s10e3R | CCATTCACAGTAGCTTACCCA | Exon 11 |
| 154 | q11e2R | TACATGAATGACATTTACAGCA | Exon 12 |
| 155 | q11i4R | AAGATGAAGACACAGTTCCC | Intron 12 |
| 156 | s12e1R | CTGGTTTAGCATGAGGCGGT | Exon 13 |
| 157 | q13-1e2R | TCGTATAGAGTTGATTGGATTGAGA | Exon 14 |
| 158 | q13-2e1R | TTCTGTGGGGTGAAATAC | Exon 14 |
| 159 | q14ae6R | CACATCCCCAAACTATCTTAA | Exon 15 |
| 160 | q14be2R | TGGATTACAATACATACAAACA | Exon16 |
| 161 | q15e4R | GGCCCTATTGATGGTGGATC | Exon 17 |
| 162 | q16e5R | AGGTAAGCAGTTCTGACTTATTA | Exon 18 |
| 163 | q17ae1R | CAGATGAGTATCGCACATTC | Exon 19 |
| 164 | q17be1R | GATAACCTATAGAATGCAGC | Exon 20 |
| 165 | q18e1R | GAAGGAAAGAAGAGATAAGG | Exon 21 |
| 166 | q19e4R | CGCTAACACATTGCTTCAGGCTAC | Exon 22 |
| 167 | q19i3R | CTTCAATGCACCTCCTCCC | Intron 22 |
| 168 | q20e4R | ACAAGTATCAAATAGCAG | Exon 23 |
| 169 | q21e2R | CAAAAGTACCTGTTGCTCCA | Exon 24 |
| 170 | q22e1R | AAGCAGGCATAATGATTC | Exon 25 |
| 171 | q23e1R | AATTACAAGGGCAATGAG | Exon 26 |
| 172 | q24e1R | GCAGAGGTAACTGTTCCAC | Exon 27 |
| 173 | CFTR-22.2F | AGTAATAAAGATGAAGACACAGTTCCC | Intron 12 |
| 174 | CFTR-31.2R | CTTCAATGCACCTCCTCCC | Intron 22 |

The following examples serve to illustrate the present invention. These examples are in no way intended to limit the scope of the invention.

EXAMPLE 5

Amplicon Library Generation

Genomic DNA was isolated from either whole blood or paraffin embedded tissue. CFTR amplicon libraries were created for samples from 48 different sources. The CFTR gene is one of a select few genes that to date has been extensively and exhaustively sequenced and, as such, has been annotated with many polymorphisms. Avoiding these polymorphism made the selection of primer and or probe binding sites particularly difficult. Libraries were generated using primers from Table 1 or Table 2 and size selected using either AMPure® beads or eGel.

The forward primers of Tables 1 and 2 each had an adapter oligonucleotide ligated to the 5' end of the primer. The adapter sequence of the forward primer adapter was 5'-ACACTGACGACATGGTTCTACA-3'. The reverse primers of Tables 1 and 2 each had an adapter oligonucleotide ligated to the 5' end of the primer. The sequence of the reverse primer adapter was 5'-TACGGTAGCAGAGACTTGGTCT-3'.

In addition, the high GC content of the CFTR promoter region made it additionally difficult to determine suitable thermal cycling conditions during library generation. The ultimate PCR protocol employed is shown in Table 3.

TABLE 3

| PCR Protocol | | |
|---|---|---|
| PCR Stages | Number of Cycles | |
| 50° C. 2 minutes | 1 | 1 |
| 70° C. 20 minutes | 1 | |
| 95° C. 10 minutes | 1 | |
| 95° C. 30 seconds | X4 | 2 |
| 65° C. 30 seconds | | |
| 72° C. 1 minute | | |
| 95° C. 15 seconds | X8 | 3 |
| 80° C. 30 seconds | | |
| 60° C. 30 seconds | | |
| 72° C. 1 minute | | |
| 95° C. 15 seconds | x8 | 4 |
| 60° C. 30 seconds | | |
| 72° 1 minute | | |
| 95° C. 15 seconds | x2 | 5 |
| 80° C. 30 seconds | | |
| 60° C. 30 seconds | | |
| 72° C. 1 minute | | |
| 95° C. 15 seconds | X12 | 6 |
| 60° C. 30 seconds | | |
| 72° C. 1 minute | | |
| 95° C. 15 seconds | X6 | 7 |
| 80° C. 30 seconds | | |
| 60° C. 30 seconds | | |
| 72° C. 1 minute | | |

That which is claimed is:

1. A method for determining the nucleotide sequence of a sample CFTR nucleic acid comprising:
    (a) producing an adapter-tagged amplicon library by amplifying multiple target segments of the sample CFTR nucleic acid, wherein each target segment is amplified with a pair of oligonucleotide primers, wherein at least one primer of the primer pair is selected from the group consisting of SEQ ID NOS: 3-8, 55-60, 107, 108, 141, and 142; and
    (b) determining the nucleotide sequences of the target segments by sequencing the amplicons in the amplicon library using high throughput massively parallel sequencing.

2. A method for determining the presence or absence of a CFTR nucleotide sequence variant in a sample CFTR nucleic acid comprising:
    (a) producing an adapter-tagged amplicon library by amplifying multiple target segments of the sample CFTR nucleic acid, wherein each target segment is amplified with a pair of oligonucleotide primers, wherein at least one primer of the primer pair is selected from the group consisting of SEQ ID NOS: 3-8, 55-60, 107, 108, 141, and 142;
    (b) determining the nucleotide sequences of the target segments by sequencing the amplicons in the amplicon library using high throughput massively parallel sequencing;
    (c) comparing each target segment nucleotide sequence determined in step (b) with the corresponding region of a reference CFTR nucleotide sequence; and
    (d) determining that the sample CFTR nucleic acid has a variant sequence if one or more of the target segment sequences is different from the corresponding region of the reference CFTR nucleotide sequence.

3. A method for determining the presence or absence of base changes, gene deletions and gene duplications in a sample CFTR nucleic acid as compared to a reference CFTR nucleotide sequence, said method comprising:
    (a) producing an adapter-tagged amplicon library by amplifying multiple target segments of the sample CFTR nucleic acid, wherein each target segment is amplified with a pair of oligonucleotide primers, wherein at least one primer of the primer pair is selected from the group consisting of SEQ ID NOS: 3-8, 55-60, 107, 108, 141, and 142;
    (b) determining the nucleotide sequences of the target segments by sequencing the amplicons using high throughput massively parallel sequencing;
    (c) comparing each target segment sequence determined in step (b) with the corresponding region of the reference CFTR nucleotide sequence; and
    (d) determining that one or more base changes, gene deletions and/or gene duplications is present in the sample CFTR nucleic acid if one or more of the target segment sequences is different from the corresponding region of the reference CFTR nucleotide sequence.

4. A method for determining a genetic basis for cystic fibrosis in an individual comprising:
    (a) producing an adapter-tagged amplicon library by amplifying multiple target segments of a CFTR nucleic acid from said individual, wherein each target segment is amplified with a pair of oligonucleotide primers, wherein at least one primer of the primer pair is selected from the group consisting of SEQ ID NOS: 3-8, 55-60, 107, 108, 141, and 142;
    (b) determining the nucleotide sequences of the target segments by sequencing the amplicons using high throughput massively parallel sequencing; and
    (c) determining that the individual has a genetic basis for cystic fibrosis if the nucleotide sequence of one or more of the target segments contains a mutation associated with cystic fibrosis.

5. The method of claim 1, wherein the multiple target segments are amplified by PCR.

6. The method of claim 1, wherein the sample CFTR nucleic acid is at least one nucleic acid selected from the group consisting of genomic DNA, mRNA and cDNA.

7. The method of claim 1, wherein an adapter sequence is ligated to one of both ends of each amplicon.

8. The method of claim 1, wherein at least one primer of the primer pair is ligated to a sequencing adapter sequence prior to amplification.

9. The method of claim 2, wherein said reference nucleotide CFTR sequence comprises a wild type CFTR nucleic acid sequence.

10. The method of claim 1, wherein the amplicons are labeled with an index label that indicates the sample source from which the amplicon is generated.

11. The method of claim 10, wherein the index label is an oligonucleotide.

12. The method of claim 1, wherein the multiple target segments of the sample CFTR nucleic acid, together, span the CFTR coding region and all intron/junctions.

13. The method of claim 12, wherein the multiple target segments further span about 1000 nucleotides of the promoter region immediately upstream of the first exon.

14. The method of claim 13, wherein the multiple target segments further span about 200 to 350 nucleotides immediately downstream of the CFTR sequence.

15. The method of claim 7, further-comprising at least one primer comprising a nucleotide sequence selected from the group consisting of SEQ ID NOs: 3-174.

16. The method of claim 1, wherein the high throughput massively parallel sequencing involves a read depth approach.

17. The method of claim 3, wherein said reference nucleotide CFTR sequence comprises a wild type CFTR nucleic acid sequence.

* * * * *